United States Patent [19]

Mauri et al.

[11] 4,163,789

[45] Aug. 7, 1979

[54] ANTI-PSYCHOTIC (CYCLOALKENYLALKYLPIPERIDINO) BENZAMIDES

[75] Inventors: Jacinto M. Mauri; Armando Vega-Noverola; Robert G. W. Spickett, all of Barcelona, Spain

[73] Assignee: Anphar, S.A., Madrid, Spain

[21] Appl. No.: 769,529

[22] Filed: Feb. 17, 1977

[30] Foreign Application Priority Data

Feb. 17, 1976 [GB] United Kingdom ............... 6207/76
Jan. 24, 1977 [GB] United Kingdom ............... 2728/77

[51] Int. Cl.$^2$ ................ A61K 31/445; C07D 211/58; C07D 211/26
[52] U.S. Cl. ............................ 424/267; 546/205; 546/223; 546/224; 546/229; 546/234
[58] Field of Search ............... 260/293.56, 293.77, 260/293.87, 293.73, 293.65, 293.78; 424/267; 546/223, 224, 229, 234

[56] References Cited

U.S. PATENT DOCUMENTS

| 3,342,826 | 9/1967 | Miller et al. ............ 260/293.77 X |
| 3,502,652 | 3/1970 | Jucker et al. ............ 260/293.77 X |
| 3,577,440 | 5/1971 | Lunsford et al. ............ 260/326.3 |
| 3,963,745 | 6/1976 | Cale et al. ............ 260/326.5 S |
| 4,021,567 | 5/1977 | Kaplan et al. ............ 260/293.73 X |

FOREIGN PATENT DOCUMENTS

| 2508045 | 9/1975 | Fed. Rep. of Germany ...... 260/293.77 |
| 1218570 | 1/1971 | United Kingdom ............... 260/293.61 |
| 1345872 | 2/1974 | United Kingdom ............... 260/293.77 |

*Primary Examiner*—Natalie Trousof
*Assistant Examiner*—Richard A. Schwartz
*Attorney, Agent, or Firm*—Morgan, Finnegan, Pine, Foley & Lee

[57] ABSTRACT

This invention relates to piperidine derivatives. More particularly, the invention relates to substituted benzoic acid amides of N-substituted piperidine and to pharmaceutical compositions thereof, which are useful in antagonizing the effects of dopamine or dopaminergic agents of endogenous or exogenous origin and in treating nausea and vomiting resulting from gastrointestinal disorders, congestive heart failure, post operative conditions, etc., other gastrointestinal disorders such as dyspepsia, flatulence, bile regurgitations, hiatus hernia, peptic ulcer, reflux aerophagitis, gastritis, duodenitis, and cholethiasis, and a variety of conditions affecting the central nervous system such as acute and chronic psychoses, maniacal psychosis, schizophrenias, serious disturbances of behavior and non-melancholic depressive state and migraine. The invention also relates to methods of preparing piperidine derivatives.

36 Claims, No Drawings

4,163,789

ANTI-PSYCHOTIC (CYCLOALKENYLALKYLPIPERIDINO) BENZAMIDES

SUMMARY OF THE INVENTION

According to one aspect of our invention, we provide compounds of the general formula

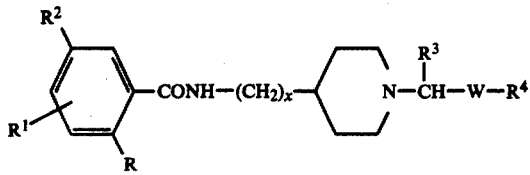

wherein R represents a lower alkoxy or lower alkenyloxy group; $R^1$ and $R^2$, which may be the same or different, each represent a hydrogen or halogen atom, or a sulphonamido, amino, lower alkylamino, di(lower)alkylamino, lower alkylsulphonyl or lower alkylsulphonamido group, or a lower acylamino group in which the acyl moiety is derived from a carboxylic acid, including halogen substituted carboxylic acids such as trifluoroacetic acid (preferably a lower alkanoylamino group), the halogen atom or group represented by the symbol $R^1$ being in the 3- or 4-position of the phenyl ring (preferably in the 4-position), with the proviso that $R^1$ and $R^2$ do not both represent hydrogen atoms; $R^3$ represents a hydrogen atom or a lower alkyl, lower alkenyl or phenyl group or a cycloalkyl or cycloalkenyl group having from 3 to 7 carbon atoms in the ring; $R^4$ represents a cycloalkyl group having from 3 to 7 carbon atoms in the ring optionally substituted by an alkyl group containing 1 to 3 carbon atoms or a hydroxy(lower)alkyl or lower alkenyl group, or $R^4$ represents an adamantyl group or a group of the formula

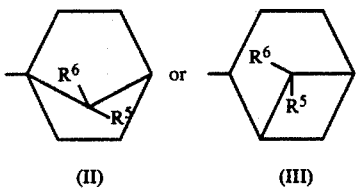

wherein $R^5$ and $R^6$ each represent a hydrogen atom or a methyl group, or a grouping of formula II or III containing a double bond between two of the carbon atoms in the cyclohexyl ring; x represents zero or 1, and W represents a single bond or a lower alkylene (e.g., —CH₂— or —CH₂CH₂—) or lower alkenylene (e.g., —CH=CH— or —CH₂—CH=CH—) group with the proviso that when W is a single bond $R^3$ is other than a cycloalkenyl group, and pharmaceutically acceptable acid addition salts and quaternary ammonium derivatives and N-oxides thereof. Preferably x represents zero and W represents a single bond.

Preferred compounds of general formula I are those of the more specific formula

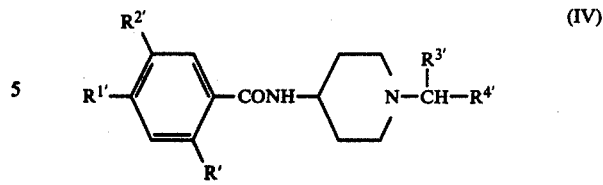

wherein R' represents a lower alkoxy (preferably methoxy or ethoxy) or allyloxy group, $R^{1'}$ represents a hydrogen atom, or an amino, lower alkylamino (preferably methylamino), di(lower)alkylamino (preferably dimethylamino) or a lower acylamino (preferably lower alkanoylamino, e.g., acetamido or trifluoroacetamido) group, $R^{2'}$ represents a halogen (preferably chlorine or bromine) atom, or an amino, sulphonamido or lower alkylsulphonyl (preferably methylsulphonyl) group, $R^{3'}$ represents a hydrogen atom or an alkyl group containing 1 to 3 carbon atoms (preferably methyl) group, and $R^{4'}$ represents a cycloalkyl group optionally substituted by a lower alkyl (preferably methyl) group and pharmaceutically acceptable acid addition salts thereof.

Of outstanding importance are N-(1-cyclohexylmethylpiperid-4-yl)-2-methoxy-4-amino-5-chlorobenzamide, N-(1-cyclohexylmethylpiperid-4-yl)-2-methoxy-4-amino-5-bromobenzamide, N-(1-cyclohexylmethylpiperid-4-yl)-2-methoxy-4-methylamino-5-chlorobenzamide, N-(1-cyclohexylmethylpiperid-4-yl)-2-allyloxy-4-amino-5-chlorobenzamide and N-(1-cyclohexylmethylpiperid-4-yl)-2-ethoxy-4-amino-5-chlorobenzamide, and their pharmaceutically acceptable acid addition salts.

According to another aspect of our invention, we provide compounds of the general formula

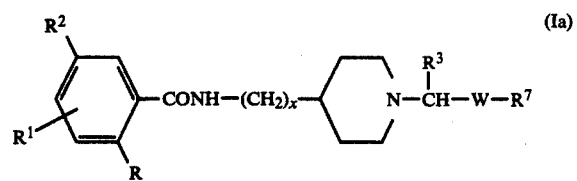

wherein R represents a lower alkoxy or lower alkenyloxy group; $R^1$ and $R^2$, which may be the same or different, each represent a hydrogen or halogen atom, or a sulphonamido, amino, lower alkylamino, di(lower)alkylamino, lower alkylsulphonyl or lower alkylsulphonamido group, or a lower acylamino group in which the acyl moiety is derived from a carboxylic acid, including halogen substituted carboxylic acids such as trifluoroacetic acid (preferably a lower alkanoylamino group), the halogen atom or group represented by the symbol $R^1$ being in the 3- or 4-position of the phenyl ring (preferably in the 4-position), with the proviso that $R^1$ and $R^2$ do not both represent hydrogen atoms; $R^3$ represents a hydrogen atom or a lower alkyl, lower alkenyl, or phenyl group, or a cycloalkyl or cycloalkenyl group having from 3 to 7 carbon atoms in the ring; $R^7$ represents a cycloalkenyl group having from 3 to 7 carbon atoms in the ring optionally substituted by an alkyl group containing 1 to 3 carbon atoms or a hydroxy(lower)alkyl or lower alkenyl group; x represents zero or 1, and W represents a single bond or a lower alkylene (e.g., —CH₂— or —CH₂CH₂—) or lower alkenylene (e.g., —CH=CH— or —CH₂—CH=CH—) group, and pharmaceutically-acceptable acid addition salts and quaternary ammonium derivatives and N-oxides thereof. Preferably x represents zero and W represents a single bond.

The qualification "lower" as applied in this specification to alkoxy, alkenyloxy, alkyl, acyl, alkanoyl, alkenyl, alkylene, and alkenylene groups means that the group in question contains at most 6 carbon atoms. It is to be understood that the cycloalkenyl groups within the definitions of R³ and R⁷ may have one, two, or three double bonds as is appropriate for the number of carbon atoms in the ring. The cycloalkenyl groups may be, for example, cyclopentenyl, cyclohexenyl and cycloheptenyl with one double bond present, cyclohexadienyl (preferably cyclohexa-1,4-dienyl optionally substituted by an alkyl group containing 1 to 3 carbon atoms), and cycloheptatrienyl.

Illustrative examples of the acylamino group include formamido, acetamido, propionamido, chloroacetamido, trifluoroacetamido, aminoacetamido, 1-piperidylacetamido, ureido, N-alkylureido, butyramido, pentanoamido, and hexanoamido.

Preferred compounds of general formula Ia are those of the more specific formula

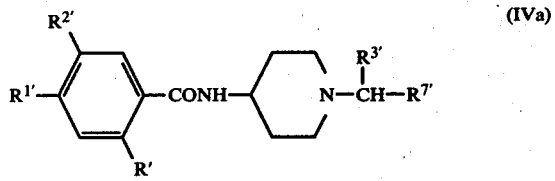

wherein R' represents a lower alkoxy (preferably methoxy or ethoxy) or allyloxy group, R¹' represents a hydrogen atom, or an amino, lower alkylamino (preferably methylamino), di(lower)alkylamino (preferably dimethylamino), or a lower acylamino (preferably lower alkanoylamino, e.g. acetamido or trifluoroacetamido) group, R²' represents a halogen (preferably chlorine or bromine) atom, or an amino, sulphonamido or lower alkylsulphonyl (preferably methylsulphonyl) group, R³' represents a hydrogen atom or a lower alkyl (preferably methyl) group and R⁷' represents a cycloalkenyl group optionally substituted by an alkyl group containing 1 to 3 carbon atoms (preferably methyl), and pharmaceutically acceptable acid addition salts thereof.

Of outstanding importance are those compounds of general formula IVa wherein R⁷' represents the cyclohexa-1,4-dienyl group optionally substituted by a methyl group and, in particular, N-[1-cyclohexa-1',4'-dienylmethylpiperid-4-yl]-2-methoxy-4-amino-5-chlorobenzamide, N-[1-cyclohexa-1',4'-dienylmethyl-piperid-4-yl]-2-methoxy-4-methylamino-5-chlorobenzamide, N-[1-cyclohexa-1',4'-dienylmethylpiperid-4-yl]-2-methoxy-4-acetamido-5-chlorobenzamide and N-[1-(4-methylcyclohexa-1,4-dienyl)methylpiperid-4-yl]-2-methoxy-4-amino-5-chlorobenzamide, and their pharmaceutically-acceptable acid addition salts.

As a further aspect of our invention, we provide pharmaceutical compositions comprising compounds of the general formulas I and Ia together with a pharmaceutically acceptable carrier or diluent.

DETAILED DESCRIPTION OF THE INVENTION

Preparation of Compounds

The piperidine derivatives of general formula I are prepared by the process which comprises reacting a reactive derivative of a benzoic acid of the general formula

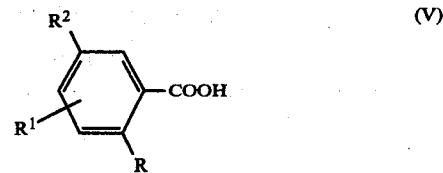

wherein R, R¹, and R² are as hereinbefore defined, with a piperidine derivative of the general formula

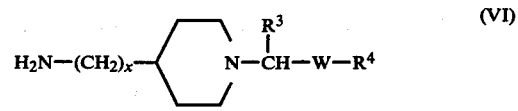

wherein the R³, R⁴, W, and x are as hereinbefore defined. The reactive derivative of the said benzoic acid may be a halide (preferably chloride), an alkyl ester (preferably methyl ester), anhydride or a mixed anhydride, the N-imidazolamide, or acid azide.

The piperidine derivatives of general formula Ia are prepared by the process which comprises reacting a reactive derivative of a benzoic acid of general formula V with a piperidine derivative of the general formula

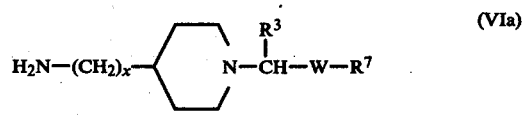

wherein R³, R⁷, W, and x are as hereinbefore defined.

The reactions are preferably carried out in the presence of an inert organic solvent, for example, benzene, toluene, chloroform, tetrahydrofuran or dioxan, at a temperature between about −5° and 120° C.

The piperidine derivatives of general formulas VI and VIa wherein x is zero can be prepared by reduction of corresponding piperid-4-one oximes with lithium aluminum hydride in the presence of diethyl ether or tetrahydrofuran, or by reductive amination of corresponding piperid-4-ones dissolved in an organic solvent, e.g., an alcohol containing up to 6 carbon atoms, in the presence of Raney nickel or platinum as catalyst. The piperidine derivatives of general formulas VI and VIa wherein R³ and/or R⁷ represent a cyclohexadienyl group can be prepared from a corresponding phenyl derivative of that formula wherein R³ and/or R⁷ represent a phenyl group by reduction with lithium in the presence of liquid ammonia or a lower alkylamine. The piperidine derivatives of general formulas VI and VIa wherein x is 1 can be prepared by know reductive methods starting from corresponding 4-cyanopiperidines.

Halides of the benzoic acids of general formula V can be prepared by reaction of the acid with thionyl chloride or a phosphorus halide in the presence of an inert organic solvent such as benzene, toluene or a halogenated hydrocarbon. Mixed anhydrides of the benzoic acids of general formula V can be prepared by the reaction of the acid with, for example, an alkyl chloroformate in the presence of an organic nitrogen-containing base, e.g., triethylamine, in an inert organic solvent, e.g., tetrahydrofuran or methylene chloride, and at a temperature between about −20° and +25° C. Esters and anhydrides of the benzoic acids of formula V, which may be employed as starting materials in the aforementioned process, can be prepared from the benzoic acids by methods known per se, as can also the N-imidazolamides or acid azides of the acids.

The piperidine derivatives of general formulas I and Ia can also be prepared, according to a further feature of the invention, by direct reaction of a benzoic acid of general formula V with a piperidine derivative of general formula VI or VIa, respectively, in the presence of an appropriate dehydrating agent. Such agents are silicon tetrachloride, a mono-, di-, or trialkyl-silyl chloride, titanium tetrachloride, N,N'-dicyclohexyl-carbodiimide, thionyl chloride, sulphur trioxide in dimethyl sulphoxide, toluene-p-sulphonyl chloride, acetone dimethyl acetal or a polymeric dehydrating agent. The reaction is carried out in an inert organic solvent, e.g., methylene chloride, acetone, pyridine, ethyl acetate or dioxan, at a temperature between 20° and 110° C.

In the preparation by the aforementioned processes of those compounds of general formulas I and Ia wherein the symbol $R^1$ and/or $R^2$ represent an amino group, it is sometimes advisable to protect the amino groups of the acid of general formula V or derivative thereof before reacting the compound with a piperidine derivative of general formula VI or VIa. In this case an N-acyl derivative of the amino-substituted benzoic acid of general formula V is initially prepared, the acyl protecting group preferably being acetyl, chloroacetyl, trifluoroacetyl or phthalimido. After the reaction between the N-acylated compound of general formula V, or reactive derivative thereof, with a piperidine derivative of general formula VI or VIa, the corresponding N-acyl derivative of the compound of general formula I or Ia is obtained and that compound is then subjected to acid or alkaline hydrolysis to give the corresponding compound of general formula I or Ia in which $R^1$ and/or $R^2$ represent an amino group. Acid hydrolysis of the N-acylated compound may be carried out by heating with dilute hydrochloric acid, preferably at the boiling point of the reaction mixture, while alkaline hydrolysis is preferably carried out at room temperature with sodium or potassium hydroxide in an aqueous-slcoholic solution.

Therapeutic Properties and Administration

The piperidine derivatives of general formulas I and Ia have as one of their principal pharmacological properties the ability to antagonize the effects of dopamine or dopaminergic agents of endogenous or exogenous origin. They have exhibited activities which may be considered beneficial in the treatment of gastrointestinal and cerebral malfunction in mammals, including man. They have also been shown to be capable of exerting anorectic properties. Their characteristic properties are an antagonism of the effects of the dopaminergic agent, apomorphine, in animals, local anaesthetic activity and the ability to induce catatonia in rats and mice. Consequently, they are useful in the treatment of nausea and vomiting of diverse origin and as neuroleptic or tranquillizing agents. They are useful for the treatment of nausea and vomiting resulting from gastrointestinal disorders, congestive heart failure, post-operative conditions, etc., other gastrointestinal disorders such as dyspepsia, flatulance, bile regurgitations, hiatus hernia, peptic ulcer, reflux aerophatitis, gastritis, duodenitis, and cholethiasis, and a variety of conditions affecting the central nervous system such as acute and chronic psychoses, maniacal psychosis, schizophrenias, serious disturbances of behavior and non-melancholic depressive states, and migraine. The compounds are also useful in the treatment of obesity and allied conditions where the administration of an appetite supressant is warranted, as an adjunct to radiography for the gastrointestinal tract, and for overcoming gastrointestinal stasis for diagnostic or therapeutic purposes.

For therapeutic purposes the piperidine derivatives of general formulas I and Ia may be employed in the form of non-toxic pharmaceutically acceptable inorganic or organic acid addition salts such as sulphates, hydrohalides, phosphates, lower alkanesulphonates, arylsulphonates, salts of aliphatic mono-, di-, or tri-basic acids of from 1 to 20 carbon atoms which may contain one or more double bonds, an aryl nucleus or other functional group such as hydroxy, amino, or keto; salts of aromatic acids in which the aromatic nucleus may optionally be substituted by groups such as hydroxy, lower alkoxy, amino, mono- or di-(lower)alkylamino, and sulphonamido groups. They may also be employed in the form of pharmaceutically acceptable quaternary ammonium salts such as those salts formed by reaction of the piperidine derivatives of general formulas I and Ia with lower alkyl halides or sulphates, or in the form of oxygenated derivatives in which oxygen is attached to the nitrogen atom of the piperidine nucleus, viz., the N-oxides.

The pharmaceutically acceptable acid addition salts and quaternary ammonium derivatives and N-oxides of the piperidine derivatives of general formulas I and Ia may be prepared by methods known per se.

Included within the scope of the present invention are pharmaceutical compositions which comprise, as active ingredient, at least one piperidine derivative of general formula I or a non-toxic pharmaceutically acceptable acid addition salt or quaternary ammonium derivative or N-oxide thereof, in association with a pharmaceutically acceptable carrier or diluent. Also included within the scope of the present invention are pharmaceutical compositions which comprise, as active ingredient, at least one piperidine derivative of general formula Ia, or a non-toxic pharmaceutically acceptable acid addition salt or quaternary ammonium derivative or N-oxide thereof, in association with a pharmaceutically acceptable carrier or diluent. Preferably the above compositions are made up in a form suitable for oral, topical, percutaneous or parenteral administration.

The pharmaceutically acceptable carriers or diluents which are admixed with the active compound, or compounds, to form the compositions of this invention are well know per se and the actual excipients used depend, inter alia, on the method of administering the compositions. Compositions of the invention may be adapted for oral, topical, percutaneous, or parental administration; however, the preferred method of administration is per os. In this case, the compositions for oral administration may take the form of tablets, capsules, lozenges, or effervescent granules or liquid preparations, such as mixtures, elixirs, syrups, or suspensions, all containing one or more compounds of the invention; such preparations may be made by methods well known in the art.

The diluents which may be used in the preparation of the composition include those liquid and solid diluents which are compatible with the active ingredients, together with, if desired, coloring or flavoring agents. Tablets or capsules may conveniently contain between about 0.1 and 20 mg, preferably between about 0.1 and 5 mg, of active ingredient or the equivalent amount of an acid addition salt or quaternary ammonium or N-oxide derivative thereof.

The liquid compositions adapted for oral use may be in the form of solutions or suspensions. The solutions may be aqueous solutions of a soluble salt or other derivative of the active compound in association with, for example, sucrose to form a syrup. The suspension may comprise a water insoluble active compound of the invention or an acid addition salt or quaternary ammonium or N-oxide derivative thereof in association with water, together with a suspending agent and flavoring agent.

Compositions for parenteral injection may be prepared from water-soluble salts, which may or may not be freeze-dried, and which may be dissolved in water or an appropriate parenteral injection fluid.

Salts of compounds of this invention would be effective in humans for the properties described above, e.g., treating nausea and/or vomiting, at single doses of between about 0.1 to 20 mg. and at daily doses of between about 0.5 and 100 mg. For example, N-(1-cyclohexyl methyl piperid-4-yl)-2-methoxy-4-amino-5-chlorobenzamide hydrochloride has been found effective in rats as follows: antiapomorphine, 12.5 mg/kg, oral; local anaesthetic, 0.3 percent; catatonia, 1 mg/kg, I.V.; and stomach emptying, 0.3 mg/kg, I.V. The same compound is effective in humans at single dosages of between 10 and 100 mg.

N-(1-cyclohex-1';4'-dienylmethylpiperid-4-yl)-2-methoxy-4-amino-5-chlorobenzamide hydrochloride has been found effective in rats as follows: antiapomorphine, 1 mg/kg, oral; local anaesthetic, 0.3 percent; catatonia, 1 mg/kg I.V.; and stomach emptying, 0.3 mg/kg I.V. The same compound is effective in humans at daily dosages of between 0.5 and 15 mg.

In another aspect of the invention, the compounds may be mixed with other active anti-acid and anti-ulcer agents (excluding anticholinergic agents) for oral or, in appropriate cases, for parenteral use.

The following examples illustrate one aspect of the invention, including preparation of piperidine derivatives and pharmaceutical compositions.

EXAMPLE 1

1. A solution of 1-cyclohexylmethylpiperid-4-one oxime (37.8 g; 0.18 moles) dissolved in anhydrous diethyl ether (250 ml) was added little by little to a suspension of lithium aluminium hydride (14.04 g; 0.36 moles) in anhydrous diethyl ether (200 ml). On completion of the addition, the resultant mixture was heated to the boiling point and maintained there under reflux for 12 hours, and then thoroughly cooled whilst water (14 ml), 15% (w/v) aqueous sodium hydroxide solution (14 ml) and water (42 ml) were added successively. The mixture was filtered and the ethereal solution was dried ($Na_2SO_4$) and the solvent removed in vacuo. The product 1-cyclohexylmethyl-4-aminopiperidine (31 g) was isolated as a viscous liquid, b.p. 105°–110° C./0.3 mm Hg.

In a similar manner, using appropriate oximes as starting materials, there were also prepared:
(a) 1-cyclopentylmethyl-4-aminopiperidine, b.p. 90°–92° C./0.45 mm Hg;
(b) 1-cyclobutylmethyl-4-aminopiperidine, b.p. 70°–71° C./0.05 mm Hg;
(c) 1-(1-adamantylmethyl)-4-aminopiperidine, m.p. 76°–79° C., and
(d) 1-(4-methylcyclohexylmethyl)-4-aminopiperidine, b.p. 127°–130° C./4 mm Hg.

2. A solution of 1-cyclohexylmethylpiperid-4-one (65 g; 0.33 moles in a saturated ethanolic solution of ammonia (350 ml) was hydrogenated in the presence of Raney nickel catalyst (6.5 g) at 75° C. and 13 atmospheres for 3.5 hours. The mixture was cooled, the catalyst filtered off and the solvent removed by distillation in vacuo. The residue was treated with a saturated ethanolic solution of hydrogen chloride, and the insoluble dihydrochloride was filtered off, treated with an aqueous solution of sodium hydroxide and extracted with chloroform. The organic layer was dried ($Na_2SO_4$) and the solvent removed in vacuo giving 1-cyclohexylmethyl-4-aminopiperidine (45.5 g) as a viscous liquid, b.p. 105°–110° C./0.3 mm Hg.

Also prepared in a similar manner were:
(a) 1-cycloheptylmethyl-4-aminopiperidine, b.p. 101°–102° C./0.15 mm Hg, and
(b) 1-cyclobutylmethyl-4-aminopiperidine, b.p. 70°–71° C./0.05 mm Hg.

EXAMPLE 2

Triethylamine (5.6 ml; 0.04 moles) and ethyl chloroformate (3.84 ml; 0.04 moles) were added successively to a stirred suspension of 2-methoxy-4-amino-5-chlorobenzoic acid (8 g; 0.04 moles) in anhydrous tetrahydrofuran (300 ml) whilst maintaining the temperature beween −5° and −10° C. After stirring at this temperature for 0.5 hours, a solution of 1-cyclohexylmethyl-4-aminopiperidine (7.85 g; 0.04 moles) in anhydrous tetrahydrofuran (50 ml) was added, the temperature was maintained at −5° to −10° C. for 1 hour and then allowed overnight to reach room temperature. The solvent of the mixture was removed in vacuo, the residue poured into water, extracted with chloroform and the organic layer washed with water. The chloroformic solution was dried ($Na_2SO_4$) and the solvent removed in vacuo to give a solid which was triturated with a mixture of methanol and diethyl ether. N-(1-Cyclohexylmethylpiperid-4-yl)-2-methoxy-4-amino-5-chlorobenzamide (8 g) was thus obtained.

The hydrochloride was prepared by addition of a saturated ethanolic solution of hydrogen chloride to a solution of the base in ethanol. Recrystallization from ethanol gave a white solid, melting point 225°–227° C. (dec).

Also prepared in a similar manner were:
(a) N-(1-cyclopentylmethylpiperid-4-yl)-2-methoxy-4-amino-5-chlorobenzamide hydrochloride, m.p. 226°–227° C.;
(b) N-(1-cyclobutylmethylpiperid-4-yl)-2-methoxy-4-amino-5-chlorobenzamide hydrochloride, m.p. 240°–242° C.;
(c) N-[1-(1-adamantyl)methylpiperid-4-yl]-2-methoxy-4-amino-5-chlorobenzamide hydrochloride, m.p. 259°–260° C.;
(d) N-(1-cycloheptylmethylpiperid-4-yl)-2-methoxy-4-amino-5-chlorobenzamide hydrochloride, m.p. 218°–220° C.;
(e) N-(1-cyclohexylmethylpiperid-4-yl)-2-methoxy-4-amino-5-bromobenzamide hydrochloride, m.p. 229°–230° C.;
(f) N-(1-cyclohexylmethylpiperid-4-yl)-2-methoxy-4-acetamido-5-chlorobenzamide hydrochloride monohydrate, m.p. 219°–221° C.;

(g) N-(1-cyclohexylmethylpiperid-4-yl)-2-methoxy-5-chlorobenzamide hydrochloride, m.p. 231°–233° C.;

(h) N-(1-chlorohexylmethylpiperid-4-yl)-2-methoxy-5-sulphonamidobenzamide hydrochloride, m.p. 237°–238° C.;

(i) N-(1-cyclohexylmethylpiperid-4-yl)-2-methoxy-4-trifluoroacetamido-5-chlorobenzamide hydrochloride, m.p. 218°–220° C. (dec);

(j) N-(1-cyclohexylmethylpiperid-4-yl)-2-methoxy-5-methylsulphonylbenzamide hydrochloride, m.p. 216°–218° C. (dec);

(k) N-[1-(4-methylcyclohexyl)methylpiperid-4-yl]-2-methoxy-4-amino-5-chlorobenzamide hydrochloride, m.p. 229°–230° C.;

(l) N-[1-(1-cyclohexyl)ethylpiperid-4-yl]-2-methoxy-4-amino-5-chlorobenzamide hydrochloride, m.p. 225°–227° C.;

(m) N-(1-cyclohexylmethylpiperid-4-yl)-2-ethoxy-4-acetamido-5-chlorobenzamide, the fumarate of which melts at 189°–191° C.;

(n) N-(1-cyclohexylmethylpiperid-4-yl)-2-ethoxy-4-amino-5-chlorobenzamide hydrochloride, m.p. 242°–243° C.;

(o) N-(1-cyclohexylmethylpiperid-4-yl)-2-methoxy-4,5-diaminobenzamide dihydrochloride, m.p. 270°–272° C. (dec);

(p) N-(1-cyclohexylmethylpiperid-4-yl)-2-methoxy-4-dimethylamino-5-chlorobenzamide, the fumarate of which melts at 187°–188° C.;

(q) N-(1-cyclohexylmethylpiperid-4-yl)-2-methoxy-4-methylamino-5-chlorobenzamide, the fumarate of which melts at 216°–218° C., and (r) N-(1-cyclohexylmethylpiperid-4-yl)-2-allyloxy-4-amino-5-chlorobenzamide hydrochloride, m.p. 212°–214° C.

The fumarates of certain piperidine derivatives indicated above were prepared by the procedure described below in Example 10 illustrating the preparation of the fumarate of N-(1-cyclohexylmethylpiperid-4-yl)-2-methoxy-4-amino-5-chlorobenzamide.

EXAMPLE 3

To a solution of 1-cyclohexylmethyl-4-aminopiperidine (9.8 g; 0.05 moles) in methyl ethyl ketone (100 ml), a solution of 2-methoxy-4-acetamido-5chlorobenzoyl chloride (14.4 g, 0.055 moles) in methyl ethyl ketone (100 ml) was slowly added at a temperature between 0° and 5° C. The mixture was stirred at the same temperature for 1 hour followed by 4 hours at room temperature. The precipitated solid was filtered off, washed with methyl ethyl ketone and recrystallized from a mixture of ethanol-water to give N-(1-cyclohexylmethylpiperid-4-yl)-2-methoxy-4-acetamido-5-chlorobenzamide hydrochloride monohydrate (21 g), m.p. 219°–221° C.

Also prepared in a similar manner was N-(1-cyclohexylmethylpiperid-4-yl)-2-methoxy-4-trifluoroacetamido-5-chlorobenzamide hydrochloride, m.p. 218°–220° C. (dec).

EXAMPLE 4

A mixture of N-(1-cyclohexylmethylpiperid-4-yl)-2-methoxy-4-acetamido-5-chlorobenzamide hydrochloride monohydrate (10 g; 0.02 moles), concentrated hydrochloric acid (6 ml) and water (20 ml) was boiled under reflux for 1.5 hours. The solution was then made alkaline with sodium hydroxide solution and extracted with chloroform. The organic solution was dried (Na$_2$SO$_4$) and the solvent removed in vacuo to give N-(1-cyclohexylmethylpiperid-4-yl)-2-methoxy-4-amino-5-chlorobenzamide (7.1 g), m.p. 213°–215° C. after recrystallization from methanol.

The base was converted into its hydrochloride by treatment with a saturated solution of ethanolic hydrogen chloride. The solid obtained melted at 225°–227° C. (dec).

EXAMPLE 5

A mixture of N-(1-cyclohexylmethylpiperid-4-yl)-2-methoxy-4-trifluoroacetamido-5-chlorobenzamide (8.1 g; 0.017 moles), ethanol (25 ml), water (15 ml) and 8 N sodium hydroxide aqueous solution (25 ml) was stirred for 12 hours at room temperature. After dilution with water, the mixture was extracted with chloroform and the chloroformic solution dried (Na$_2$SO$_4$) and evaporated in vacuo. N-(1-Cyclohexylmethylpiperid-4-yl)-2-methoxy-4-amino-5-chlorobenzamide (5 g) was obtained. It was converted into its hydrochloride by treatment with a saturated solution of ethanolic hydrogen chloride; the hydrochloride melted at 225°–227° C. (dec).

EXAMPLE 6

A mixture of methyl 2-methoxy-4-acetamido-5-chlorobenzoate (25.7 g; 0.1 moles), xylene (80 ml), 1-cyclohexylmethyl-4-aminopiperidine (21.6 g; 0.11 moles) and aluminium isopropoxide (5 g) was heated to the boiling point whilst methanol was distilled off as it was formed. When the theoretical quantity of methanol was removed, the xylene was distilled off and the residue was dissolved in 2 N hydrochloric acid (200 ml). The aqueous solution was made alkaline with sodium hydroxide solution, extracted with chloroform and the chloroformic layer evaporated to dryness to give N-(1-cyclohexylmethylpiperid-4-yl)-2-methoxy-4-acetamido-5-chlorobenzamide (27 g). Its hydrochloride monohydrate was prepared by the procedure described in Example 2, m.p. 219°–221° C.

EXAMPLE 7

N,N'-dicyclohexylcarbodiimide (10.3 g; 0.05 moles) and 1-cyclohexylmethyl-4-aminopiperidine (9.8 g; 0.05 moles) were added successively to a solution of 2-methoxy-4-acetamido-5-chlorobenzoic acid (12.1 g; 0.05 moles) in methylene chloride (250 ml). After stirring overnight at room temperature, the insoluble N,N'-dicyclohexylurea was filtered off, the solution was washed with water, dried (Na$_2$SO$_4$) and the solvent removed in vacuo. The residue was recrystallized and the product converted into its hydrochloride to give 14.2 g of N-(1-cyclohexylmethylpiperid-4-yl)-2-methoxy-4-acetamido-5-chlorobenzamide hydrochloride monohydrate, m.p. 219°–221° C.

EXAMPLE 8

To a warm solution of N-(1-cyclohexylmethylpiperid-4-yl)-2-methoxy-4-acetamido-5-chlorobenzamide (10 g; 0.023 moles) in diethyl ether (300 ml) a solution of methyl iodide (1.8 ml; 0.033 moles) in diethyl ether (25 ml) was added. The mixture was stirred at room temperature for 1 hour and then heated under reflux for 2 hours. An additional amount of methyl iodide (1 g; 0.0023 moles) was added and the reflux of the mixture was kept up for 3 more hours. The mixture was then evaporated in vacuo and the residue recrystallized from a mixture of diethyl ether-ethanol. N-(1-Cyclohexylmethylpiperid-4-yl)-2-methoxy-4-acetamido-5-chlorobenzamide methyl iodide (10.5 g), m.p. 209°–211° C., was thus obtained.

EXAMPLE 9

To a solution of N-(1-cyclohexylmethylpiperid-4-yl)-2-methoxy-4-acetamido-5-chlorobenzamide (10 g; 0.023 moles) in glacial acetic acid (50 ml) a 30% hydrogen peroxide solution (6 ml) was added. The mixture was heated for 8 hours at a temperature between 70° and 80° C. Afterwards the solvent was evaporated in vacuo, and N-(1-cyclohexylmethylpiperid-4-yl)-2-methoxy-4-acetamido-5-chlorobenzamide N-oxide was obtained as a viscous liquid. After recrystallisation from a mixture of acetone and diethyl ether, there was obtained 7.3 g of the N-oxide, melting at 206°–208° C.

EXAMPLE 10

To a hot solution of N-(1-cyclohexylmethylpiperid-4-yl)-2-methoxy-4-amino-5-chlorobenzamide (5 g; 0.013 moles) in ethanol (30 ml) there was added fumaric acid (1.7 g; 0.014 moles). The hot mixture was stirred until complete dissolution. After cooling N-(1-cyclohexylmethylpiperid-4-yl)-2-methoxy-4-amino-5-chlorobenzamide fumarate crystallized: yield 6.3 g, m.p. 229°–231° C.

EXAMPLE 11

100,000 Tablets each containing 2 mg of N-(1-cyclohexylmethylpiperid-4-yl)-2-methoxy-4-amino-5-chlorobenzamide hydrochloride were prepared from the following formulation:

| | |
|---|---|
| N-(1-cyclohexylmethylpiperid-4-yl)-2-methoxy-4-amino-5-chlorobenzamide hydrochloride | 200 g |
| microcrystalline cellulose | 1870 g |
| lactose spray dried | 9880 g |
| carboxymethyl starch | 430 g |
| sodium stearyl fumarate | 60 g |
| colloidal silicon dioxide | 60 g |

PROCEDURE

All the powders were passed through a screen with an opening of 0.6 mm. They were then all mixed in a suitable mixer for 20 minutes and compressed into 125 mg tablets using 6 mm. discs and flat bevelled punches. The disintegration time of the tablets was about 60 seconds.

EXAMPLE 12

100,000 Capsules each containing 1 mg of N-(1-cyclohexylmethylpiperid-4-yl)-2-methoxy-4-amino-5-chlorobenzamide hydrochloride were prepared from the following formulation:

| | |
|---|---|
| N-(1-cyclohexylmethylpiperid-4-yl)-2-methoxy-4-amino-5-chlorobenzamide hydrochloride | 100 g |
| lactose | 9000 g |
| sodium lauryl sulphate | 370 g |
| corn starch | 8000 g |
| alpine talc | 530 g |

PROCEDURE

The above ingredients were sieved through a 40 mesh sieve, then mixed in a suitable mixer and distributed into 100,000 gelatine capsules (180 mg).

EXAMPLE 13

10,000 Suppositories each containing 5 mg of N-(1-cyclohexylmethylpiperid-4-yl)-2-methoxy-4-amino-5-chlorobenzamide hydrochloride were prepared as follows:

| | |
|---|---|
| N-(1-cyclohexylmethylpiperid-4-yl)-2-methoxy-4-amino-5-chlorobenzamide hydrochloride | 50 g |
| theobroma oil | 19950 g |

PROCEDURE

The theobroma oil was melted and the N-(1-cyclohexylmethylpiperid-4-yl)-2-methoxy-4-amino-5-chlorobenzamide hydrochloride suspended in it. The mixture was then poured into appropriate suppository molds to make 2.0 g suppositories.

PROCEDURE 50,000 Ampoules each containing 2 mg of N-(1-cyclohexylmethylpiperid-4-yl)-2-methoxy-4-amino-5-chlorobenzamide hydrochloride were prepared from the following formulation:

| | |
|---|---|
| N-(1-cyclohexylmethylpiperid-4-yl)-2-methoxy-4-amino-5-chlorobenzamide hydrochloride | 100 g |
| sodium chloride | 500 g |
| water injectable grade q.s. | 100 liters |

PROCEDURE

The N-(1-cyclohexylmethylpiperid-4-yl)-2-methoxy-4-amino-5-chlorobenzamide hydrochloride and the sodium chloride were dissolved in approximately 80 liters of water with slight heating. The solution was diluted with water to 100 liters, passed through a bacteria-retaining filter and filled into 2 ml glass ampoules in known manner. The production of the injectable solution can take place under sterile conditions. It is also possible to work under normal conditions and then to heat-sterilize the filled ampoules.

EXAMPLE 15

1,000 Bottles of 150 ml each containing 75 mg of N-(1-cyclohexylmethylpiperid-4-yl)-2-methoxy-4-amino-5-chlorobenzamide hydrochloride were prepared as follows:

| | |
|---|---|
| N-(1-cyclohexylmethylpiperid-4-yl)-2-methoxy-4-amino-5-chlorobenzamide hydrochloride | 75 g |
| sorbitol | 70000 g |
| sorbic acid | 125 g |
| citric acid | 125 g |
| distilled water q.s. | 150 liters |
| flavouring agent | q.s. |

PROCEDURE

The N-(1-cyclohexylmethylpiperid-4-yl)-2-methoxy-4-amino-5-chlorobenzamide hydrochloride and the sorbic acid were dissolved in 100 liters of water and then the sorbitol, citric acid and flavouring agent were added with stirring until dissolution. The mixture was diluted to 150 liters and divided amongst the bottles.

Similar compositions to those described in Examples 11 to 15 can be prepared having as the active ingredient piperidine derivatives of general formula I other than N-(1-cyclohexylmethylpiperid-4-yl)-2-methoxy-4-amino-5-chlorobenzamide, for example other products conforming to that formula mentioned in Examples 2, 3, and 6 to 9.

The following examples illustrate a second aspect of the invention, including preparation of piperidine derivatives and pharmaceutical compositions:

EXAMPLE 16

A solution of lithium (5 g; 0.7 moles) in liquid ammonia (250 ml) was added little by little to another solution of 1-benzyl-4-aminopiperidine (50 g; 0.264 moles) in anhydrous diethyl ether (100 ml. After stirring for half an hour, absolute ethanol (180 ml) was added little by little, the solvent removed in vacuo and the residue taken up with water. The aqueous solution was extracted with diethyl ether and the organic layers dried and distilled in vacuo to give 1-cyclohexa-1',4'-dienyl-methyl-4-aminopiperidine (48 g), b.p. 117°–118° C./0.5 mm.Hg.

Also prepared in a similar manner were:
(a) 1-(4-methylcyclohexa-1,4-dienyl)methyl-4-aminopiperidine, b.p. 104°–106° C./0.07 mm.Hg.;
(b) 1-(1-cyclohexa-1',4'-dienyl-ethyl)-4-aminopiperidine, b.p. 103°–105° C./0.08 mm.Hg. and
(c) 1-cyclohexen-3'-ylmethyl-4-aminopiperidine, b.p. 101°–103° C./0.05 mm Hg.

EXAMPLE 17

Triethylamine (7.0 ml; 0.05 moles) and ethyl chloroformate (4.8 ml; 0.05 moles) were added successively to a stirred suspension of 2-methoxy-4-amino-5-chlorobenzoic acid (10.1 g; 0.05 moles) in anhydrous tetrahydrofuran (300 ml) whilst maintaining the temperature between −5° and −10° C. After stirring at this temperature for 0.5 hours, a solution of 1-cyclohexa-1',4'-dienyl-methyl-4-aminopiperidine (9.6 g; 0.05 moles) in anhydrous tetrahydrofuran (50 ml) was added; the temperature was maintained at −5° to −10° C. for 1 hour and then the reaction mixture was allowed to stand overnight at room temperature. The solvent was removed in vacuo, the residue poured into water, extracted with chloroform and the organic layers washed with water. The chloroform solution was dried (Na₂SO₄) and the solvent removed in vacuo to give a solid which was triturated with a mixture of methanol and diethyl ether. N-(1-cyclohexa-1',4'-dienylmethylpiperid-4-yl)-2-methoxy-4-amino-5-chlorobenzamide (12.2 g.) was obtained.

The hydrochloride monohydrate was prepared by addition of a saturated ethanolic solution of hydrogen chloride to a solution of the base in ethanol. Recrystallization of the precipitate from ethanol gave a white solid, m.p. 226°–227° C. (dec.).

Also prepared in a similar manner were:
(a) N-(1-cyclohexa-1',4'-dienylmethylpiperid-4-yl)-2-methoxy-5-methylsulphonylbenzamide hydrochloride, m.p. 209°–211° C. (dec.);
(b) N-(b 1-cyclohexa-1',4'-dienylmethylpiperid-4-yl)-2-methoxy-5-chlorobenzamide hydrochloride, m.p. 231°–233° C.;
(c) N-(1-cyclohexa-1',4'-dienylmethylpiperid-4-yl)-2-methoxy-4-amino-5-bromobenzamide hydrochloride, m.p. 215° C. (dec.);
(d) N-(1-cyclohexa-1',4'-dienylmethylpiperid-4-yl)-2-methoxy-5-sulphonamidobenzamide hydrochloride, m.p. 230°–231° C. (dec.);
(e) N-(1-cyclohexa-1',4'-dienylmethylpiperid-4-yl)-2-methoxy-4-acetamido-5-chlorobenzamide hydrochloride monohydrate, m.p. 193°–195° C.;
(f) N-[1-(4-methylcyclohexa-1,4-dienyl)methyl-piperid-4-yl]-2-methoxy-4-amino-5-chlorobenzamide hydrochloride, m.p. 246°–248° C. (dec.);
(g) N-[1-(1-cyclohexa-1',4'-dienylethyl)piperid-4-yl]-2-methoxy-4-amino-5-chlorobenzamide hydrochloride, m.p. 241°–242° C. (dec.);
(h) N-[1-(1-cyclohexa-1',4'-dienylethyl)piperidy-4-yl]-2-ethoxy-4-acetamido-5-chlorobenzamide, the fumarate of which melts at 171°–173° C.;
(i) N-[1-(1-cyclohexa-1',4'-dienylethyl)piperid-4-yl]-2-ethoxy-4-amino-5-chlorobenzamide hydrochloride, m.p. 264°–266° C.;
(j) N-(1-cyclohexa-1',4'-dienylmethylpiperid-4-yl)-2-methoxy-4,5-diaminobenzamide dihydrochloride monohydrate, m.p. 240°–242° C.;
(k) N-(1-cyclohexa-1',4'-dienylmethylpiperid-4-yl)-2-methoxy-4-dimethylamino-5-chlorobenzamide, the fumarate of which melts at 182°–184° C.;
(l) N-(1-cyclohexa-1',4'-dienylmethylpiperid-4-yl)-2-methoxy-4-methylamino-5-chlorobenzamide, the fumarate of which melts at 203°–205° C.;
(m) N-(1-cyclohexa-1',4'-dienylmethylpiperid-4-yl)-2-allyloxy-4-amino-5-chlorobenzamide hydrochloride, m.p. 180°–182° C.;
(n) N-(1-cyclohexa-1',4'-dienylmethylpiperid-4-yl)-2-ethoxy-4-amino-5-chlorobenzamide hydrochloride, m.p. 247°–249° C.;
(o) N-(1-cyclohexa-1',4'-dienylmethylpiperid-4-yl)-2-ethoxy-4-acetamido-5-chlorobenzamide, the fumarate of which melts at 173°–175° C.; and
(p) N-(1-cyclohexen-3'-ylmethylpiperid-4-yl)-2-methoxy-4-amino-5-chlorobenzamide, m.p. 189°–191° C.

The fumarates of the piperidine derivatives mentioned above were obtained by adding fumaric acid to a hot ethanolic solution of the piperidine base, the amount of added acid being substantially equimolecular to that of the piperidine base present, stirring the hot mixture until dissolution, and then cooling the resulting solution to crystallize the fumarate.

EXAMPLE 18

To a warm solution of N-(1-cyclohexen-3'-ylmethyl-piperid-4-yl)-2-methoxy-4-amino-5-chlorobenzamide (3.5 g; 0.0093 moles) in acetone (75 ml) a solution of methyl iodide (2.63 g; 0.0185 moles) in acetone (25 ml) was slowly added. The mixture was stirred at room temperature for 12 hours and then heated under reflux for 4 more hours. The mixture was then concentrated in vacuo to a small volume and the residue filtered off to give N-(1-cyclohexen-3'-ylmethylpiperid-4-yl)-2-methoxy-4-amino-5-chlorobenzamide methyl iodide (4 g.), m.p. 231°–233° C. (dec.) after recrystallization from a mixture of ethanol-water.

EXAMPLE 19

100,000 Tablets each containing 2 mg of N-(1-cyclohexa-1',4'-dienylmethylpiperid-4-yl)-2-methoxy-4-amino-5-chlorobenzamide hydrochloride monohydrate were prepared from the following formulation:

N-(1-cyclohexa-1',4'-dienylmethylpiperid-4-yl)-
2-methoxy-4-amino-5-chlorobenzamide hydrochloride
monohydrate                                    200 g

| | |
|---|---|
| microcrystalline cellulose | 1870 g |
| lactose spray dried | 9880 g |
| carboxymethyl starch | 430 g |
| sodium stearyl fumarate | 60 g |
| colloidal silicon dioxide | 60 g |

PROCEDURE

All the powders were passed through a screen with an opening of 0.6 mm. They were then all mixed in a suitable mixer for 20 minutes and compressed into 125 mg tablets using 6 mm discs and flat bevelled punches. The disintegration time of the tablets was about 60 seconds.

EXAMPLE 20

100,000 Capsules each containing 1 mg of N-(1-cyclohexa-1',4'-dienylmethylpiperid-4-yl)-2-methoxy-4-amino-5-chlorobenzamide hydrochloride monohydrate were prepared from the following formulation:

| | |
|---|---|
| N-(1-cyclohexa-1',4'-dienylmethyl(piperid-4-yl)-2-methoxy-4-amino-5-chlorobenzamide hydrochloride monohydrate | 100 g |
| lactose | 9000 g |
| sodium lauryl sulphate | 370 g |
| corn starch | 8000 g |
| alpine talc | 530 g |

PROCEDURE

The above ingredients were sieved through a 40 mesh sieve, then mixed in a suitable mixer and distributed into 100,000 gelatine capsules (180 mg).

EXAMPLE 21

10,000 Suppositories each containing 5 mg of N-(1-cyclohexa-1',4'-dienylmethylpiperid-4-yl)-2-methoxy-4-amino-5-chlorobenzamide hydrochloride monohydrate were prepared as follows:

| | |
|---|---|
| N-(1-cyclohexa-1',4'-dienylmethylpiperid-4-yl)-2-methoxy-4-amino-5-chlorobenzamide hydrochloride monohydrate | 50 g |
| theobroma oil | 19950 g |

PROCEDURE

The theobroma oil was melted and the N-(1-cyclohexa-1',4'-dienylmethylpiperid-4-yl)-2-methoxy-4-amino-5-chlorobenzamide hydrochloride monohydrate suspended in it. The mixture was then poured into appropriate suppository moulds to make 2.0 g suppositories.

EXAMPLE 22

50,000 Ampoules each containing 2 mg of N-(1-cyclohexa-1',4'-dienylmethylpiperid-4-yl)-2-methoxy-4-amino-5-chlorobenzamide hydrochloride monohydrate were prepared from the following formulation:

| | |
|---|---|
| N-(1-cyclohexa-1',4'-dienylmethylpiperid-4-yl)-2-methoxy-4-amino-5-chlorobenzamide hydrochloride monohydrate | 100 g |
| sodium chloride | 500 g |
| water injectable grade q.s. | 100 liters |

PROCEDURE

The N-(1-cyclohexa-1',4'-dienylmethylpiperid-4-yl)-2-methoxy-4-amino-5-chlorobenzamide hydrochloride monohydrate and the sodium chloride were dissolved in approximately 80 liters of water with slight heating. The solution was diluted with water to 100 liters passed through a bacteria-retaining filter and filled into 2 ml glass ampoules in known manner. The production of the injectable solution can take place under sterile conditions. It is also possible to work under normal conditions and then to heat-sterilize the filled ampoules.

EXAMPLE 23

1,000 Bottles of 150 ml each containing 75 mg of N-(1-cyclohexa-1',4'-dienylmethylpiperid-4-yl)-2-methoxy-4-amino-5-chlorobenzamide hydrochloride monohydrate were prepared as follows:

| | |
|---|---|
| N-(1-cyclohexa-1',4'-dienylmethylpiperid-4-yl)-2-methoxy-4-amino-5-chlorobenzamide hydrochloride monohydrate | 75 g |
| sorbitol | 70000 g |
| sorbic acid | 125 g |
| citric acid | 125 g |
| distilled water q.s. | 150 liters |
| flavouring agent | q.s. |

PROCEDURE

The N-(1-cyclohexa-1',4'-dienylmethylpiperid-4-yl)-2-methoxy-4-amino-5-chlorobenzamide hydrochloride monohydrate and the sorbic acid were dissolved in 100 liters of water and then the sorbitol, citric acid and flavouring agent were added with stirring until dissolution. The mixture was diluted to 150 liters and divided amongst the bottles.

Similar compositions to those described in Examples 19 to 23 can be prepared having as the active ingredient piperidine derivatives of general formula Ia other than N-(1-cyclohexa-1',4'-dienylmethylpiperid-4-yl)-2-methoxy-4-amino-5-chlorobenzamide, for example other products conforming to that formula mentioned in Example 17.

The piperidine derivatives of formulas VI and VIa are new compounds and as such constitute another feature of the present invention. The pharmacological activity of certain of the present compounds has been measured and is set forth in Table I as follows:

TABLE I

| | | | | | | | Antiapomorphine in rats* anaesthet.** | Local in rats*** | Catatonia |
|---|---|---|---|---|---|---|---|---|---|
| No. | R' | $R^{1'}$ | $R^{2'}$ | $R^{3'}$ | $R^{4'}$ or $R^{7'}$ | Derivative | | | |
| 1 | MeO | $NH_2$ | Cl | H | Cyclohexyl | Hydrochloride | +++ | ++ | ++ |
| 2 | MeO | $NH_2$ | Cl | H | Cyclopentyl | Hydrochloride | + | ++ | + |
| 3 | MeO | $NH_2$ | Cl | H | Cyclobutyl | Hydrochloride | + | ++ | + |

FORMULA IV or IVa

TABLE I-continued

FORMULA IV or IVa

| No. | R' | R¹' | R²' | R³' | R⁴' or R⁷' | Derivative | Antiapomorphine in rats* | Local anaesthet.** in rats*** | Catatonia |
|---|---|---|---|---|---|---|---|---|---|
| 4 | MeO | NH₂ | Cl | H | Adamantyl | Hydrochloride | − | ++ | − |
| 5 | MeO | NH₂ | Cl | H | Cycloheptyl | Hydrochloride | + | ++ | − |
| 6 | MeO | NH₂ | Br | H | Cyclohexyl | Hydrochloride | ++ | ++ | ++ |
| 7 | MeO | AcNH | Cl | H | Cyclohexyl | Hydrochloride monohydrate | +++ | ++ | + |
| 8 | MeO | H | Cl | H | Cyclohexyl | Hydrochloride | + | ++ | + |
| 9 | MeO | H | SO₂NH₂ | H | Cyclohexyl | Hydrochloride | − | + | − |
| 10 | MeO | F₃C-CONH | Cl | H | Cyclohexyl | Hydrochloride | ++ | ++ | ++ |
| 11 | MeO | NH₂ | Cl | H | 1,4-Cyclohexadienyl | Hydrochloride monohydrate | +++++ | ++ | ++ |
| 12 | MeO | H | SO₂CH₃ | H | 1,4-Cyclohexadienyl | Hydrochloride | + | − | − |
| 13 | MeO | H | Cl | H | 1,4-Cyclohexadienyl | Hydrocholoride | − | ++ | ++ |
| 14 | MeO | NH₂ | Br | H | 1,4-Cyclohexadienyl | Hydrochloride | − | ++ | ++ |
| 15 | MeO | H | SO₂NH₂ | H | 1,4-Cyclohexadienyl | Hydrochloride | − | ++ | − |
| 16 | MeO | AcNH | Cl | H | 1,4-Cyclohexadienyl | Hydrochloride monohydrate | ++++ | − | ++ |
| 17 | MeO | NH₂ | Cl | H | 4-Methyl-Cyclohexadienyl | Hydrochloride | +++++ | ++ | + |
| 18 | MeO | NH₂ | Cl | H | 4-Methyl-Cyclohexyl | Hydrochloride | + | NT | + |
| 19 | MeO | NH₂ | Cl | CH₃ | 1,4-Cyclohexadienyl | Hydrochloride | ++ | ++ | + |
| 20 | EtO | AcNH | Cl | H | Cyclohexyl | Fumarate | + | ++ | − |
| 21 | EtO | NH₂ | Cl | H | Cyclohexyl | Hydrochloride | ++ | ++ | + |
| 22 | EtO | AcNH | Cl | CH₃ | 1,4-Cyclohexadienyl | Fumarate | + | ++ | − |
| 23 | EtO | NH₂ | Cl | CH₃ | 1,4-Cyclohexadienyl | Hydrochloride | + | ++ | + |
| 24 | MeO | AcNH | Cl | H | Cyclohexyl | Methyliodide | − | + | − |
| 25 | MeO | AcNH | Cl | H | Cyclohexyl | N-Oxide | ++ | NT | − |
| 26 | MeO | CH₃NH | Cl | H | Cyclohexyl | Fumarate | ++++ | NT | NT |
| 27 | MeO | CH₃NH | Cl | H | 1,4-Cyclohexadienyl | Fumarate | +++++ | NT | NT |
| 28 | Alloyl-O | NH₂ | Cl | H | Cyclohexyl | Hydrochloride | + | NT | NT |
| 29 | Alloyl-O | NH₂ | Cl | H | 1,4-Cyclohexadienyl | Hydrochloride | ++ | NT | NT |
| | Metoclopramide | | | | | | +++ | + | − |

*Antiapomorphine activity in rats scored as follows:
+ active at 50 mg/Kg p.os
++ active at 25
+++ active at 12,5
++++ active at 6,25 or less
+++++ active at 3,125 or less
− not active at 50 mg/Kg
NT = not tested
** + Active at 1% i.m.
++ Active at 0.3% i.m.
*** + At least 2/3 rats show catatonia at 5 mg Kg⁻¹ i.v.
++ At least 2/3 rats show catatonia at 1 mg Kg⁻¹ i.v.

We claim:
1. A piperidine derivative of the general formula

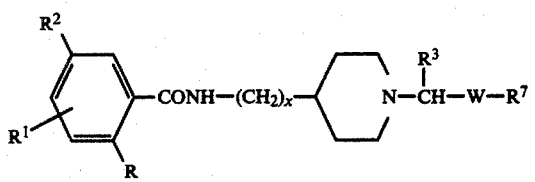

(Ia)

wherein R represents a lower alkoxy or lower alkenyloxy group; R¹ and R², which may be the same or different, each represent a hydrogen or halogen atom, or a sulphonamido, amino, lower alkylamino, di(lower)alkylamino, lower alkylsulphonyl, or lower alkylsulphonamido group, or a lower acylamino group in which the acyl moiety is derived from a carboxylic acid, the halogen atom or group represented by the symbol R¹ being in the 3- or 4-position of the phenyl ring, with the proviso that R¹ and R² do not both represent hydrogen atoms; R³ represents a hydrogen atom or a lower alkyl, lower alkenyl, or phenyl group, or a cycloalkyl or cycloalkenyl group having from 3 to 7 carbon atoms in the ring; R⁷ represents a cycloalkenyl group having from 3 to 7 carbon atoms in the ring, unsubstituted or substituted by an alkyl group containing from 1 to 3 carbon atoms or a hydroxy(lower)alkyl or lower alkenyl group; x represents zero or 1, and W represents a single bond or a lower alkylene or lower alkenylene group, or a pharmaceutically acceptable acid addition salt or a quaternary ammonium derivative or an N-oxide thereof.

2. A piperidine derivative of claim 1 wherein x represents zero and W represents a single bond.

3. A piperidine derivative of claim 1 in which R¹ represents a halogen atom, or a sulphonamido, amino, lower alkylamino, di(lower)alkylamino, lower alkylsulphonyl, lower alkylsulphonamido, or lower acylamino group, and in which R¹ is in the 4-position of the phenyl ring.

4. A piperidine derivative of claim 1 wherein R⁷ represents the cyclohexa-1,4-dienyl group unsubstituted or substituted by an alkyl group containing 1 to 3 carbon atoms.

5. A piperidine derivative of the general formula

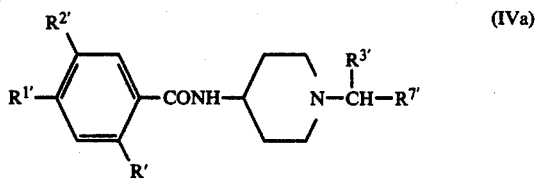

(IVa)

wherein R' represents a lower alkoxy or allyloxy group, R¹' represents a hydrogen atom, or an amino, lower alkylamino, di(lower)alkylamino or a lower acylamino group in which the acyl moiety is derived from a carboxylic acid, R²' represents a halogen atom, or an amino, sulphonamido or lower alkylsulphonyl group, R³' represents a hydrogen atom or a lower alkyl group, and R⁷' represents a cycloalkenyl group having from 3 to 7 carbon atoms in the ring, unsubstituted or substituted by an alkyl group containing 1 to 3 carbon atoms, or a pharmaceutically acceptable acid addition salt thereof.

6. A piperidine derivative of claim 5 wherein R' when a lower alkoxy group represents methoxy or ethoxy; R¹' (i) when a lower alkylamino group represents methylamino, (ii) when a di(lower)alkylamino group represents dimethylamino, or (iii) when a lower acylamino group represents a lower alkanoylamino group; R²' (i) when a halogen atom represents chlorine or bromine, or (ii) when a lower alkylsulphonyl group represents methylsulphonyl; R³' when a lower alkyl group represents methyl; and R⁷' represents a cycloalkenyl group unsubstituted or substituted by a methyl group, or a pharmaceutically acceptable acid addition salt thereof.

7. A piperidine derivative of claim 5 wherein R¹' represents the acetamido or trifluoroacetamido group.

8. A piperidine derivative of claim 5 wherein R⁷' represents the cyclohexa-1,4-dienyl group optionally substituted by a methyl group.

9. A piperidine derivative of claim 1 wherein R⁷ represents a cyclopentenyl, cyclohexadienyl or cycloheptenyl group, or a cyclohexenyl group unsubstituted or substituted in the 4-position by an alkyl group containing 1 to 3 carbon atoms or a hydroxy(lower)alkyl or lower alkenyl group, and wherein W represents a group —(CH₂)ᵧ— in which y represents zero or an integer from 1 to 5.

10. N-(1-Cyclohexa-1',4'-dienylmethylpiperid-4-yl)-2-methoxy-4-amino-5-chlorobenzamide or a pharmaceutically acceptable acid addition salt thereof.

11. N-(1-Cyclohexa-1',4'-dienylmethylpiperid-4-yl)-2-methoxy-4-acetamido-5-chlorobenzamide or a pharmaceutically acceptable acid addition salt thereof.

12. N-[1-(4-Methylcyclohexa-1,4-dienyl)methylpiperid-4-yl]-2-methoxy-4-amino-5-chlorobenzamide or a pharmaceutically acceptable acid addition salt thereof.

13. N-(1-Cyclohexa-1',4'-dienylmethylpiperid-4-yl)-2-methoxy-5-methylsulphonylbenzamide or a pharmaceutically acceptable acid addition salt thereof.

14. N-(1-Cyclohexa-1',4'-dienylmethylpiperid-4-yl)-2-methoxy-5-chlorobenzamide or a pharmaceutically acceptable acid addition salt thereof.

15. N-(1-Cyclohexa-1',4'-dienylmethylpiperid-4-yl)-2-methoxy-4-amino-5-bromobenzamide or a pharmaceutically acceptable acid addition salt thereof.

16. N-(1-Cyclohexa-1',4'-dienylmethylpiperid-4-yl)-2-methoxy-5-sulphonamidobenzamide or a pharmaceutically acceptable acid addition salt thereof.

17. N-[1-(1-Cyclohexa-1',4'-dienylethyl)piperid-4-yl]-2-methoxy-4-amino-5-chlorobenzamide or a pharmaceutically acceptable acid addition salt thereof.

18. N-[1-(1-Cyclohexa-1',4'-dienylethyl)piperid-4-yl]-2-ethoxy-4-acetamido-5-chlorobenzamide or a pharmaceutically acceptable acid addition salt thereof.

19. N-[1-(1-Cyclohexa-1',4'-dienylethyl)piperid-4-yl]-2-ethoxy-4-amino-5-chlorobenzamide or a pharmaceutically acceptable acid addition salt thereof.

20. N-(1-Cyclohexa-1',4'-dienylmethylpiperid-4-yl)-2-methoxy-4,5-diaminobenzamide or a pharmaceutically acceptable acid addition salt thereof.

21. N-(1-Cyclohexa-1',4'-dienylmethylpiperid-4-yl)-2-methoxy-4-dimethylamino-5-chlorobenzamide or a pharmaceutically acceptable acid addition salt thereof.

22. N-(1-Cyclohexa-1',4'-dienylmethylpiperid-4-yl)-2-methoxy-4-methylamino-5-chlorobenzamide or a pharmaceutically acceptable acid addition salt thereof.

23. N-(1-Cyclohexa-1',4'-dienylmethylpiperid-4-yl)-2-allyloxy-4-amino-5-chlorobenzamide or a pharmaceutically acceptable acid addition salt thereof.

24. N-(1-Cyclohexa-1',4'-dienylmethylpiperid-4-yl)-2-ethoxy-4-amino-5-chlorobenzamide or a pharmaceutically acceptable acid addition salt thereof.

25. N-(1-Cyclohexa-1',4'-dienylmethylpiperid-4-yl)-2-ethoxy-4-acetamido-5-chlorobenzamide or a pharmaceutically acceptable acid addition salt thereof.

26. N-(1-Cyclohexen-3'-ylmethylpiperid-4-yl)-2-methoxy-4-amino-5-chlorobenzamide or a pharmaceutically acceptable acid addition salt thereof.

27. A piperidine derivative of the general formula

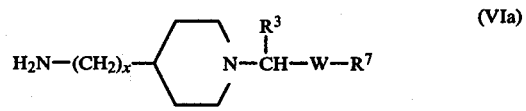

(VIa)

wherein R³, R⁷, x, and W are as defined in claim 1.

28. 1-Cyclohexa-1',4'-dienylmethyl-4-aminopiperidine, 1-(4-methylcyclohexa-1,4-dienyl)methyl-4-aminopiperidine, 1-(1-cyclohexa-1',4'-dienyl-ethyl)-4-aminopiperidine, or 1-cyclohexen-3'-ylmethyl-4-aminopiperidine.

29. An anti-psychosis composition which comprises, as active ingredient, an effective anti-psychosis amount of one or more piperidine derivatives of claim 1 and a non-toxic, pharmaceutically acceptable carrier or diluent.

30. An anti-psychosis composition which comprises, as active ingredient, an effective anti-psychosis amount of one or more compounds of claim 5 and a non-toxic, pharmaceutically acceptable carrier or diluent.

31. An anti-psychosis composition which comprises, as active ingredient, an effective anti-psychosis amount of one or more piperidine derivatives of claim 9 and a non-toxic, pharmaceutically acceptable carrier or diluent.

32. An anti-psychosis composition which comprises, as active ingredient, an effective anti-psychosis amount of a compound selected from the following group:
(a) N-(1-Cyclohexa-1',4'-dienylmethylpiperid-4-yl)-2-methoxy-4-amino-5-chlorobenzamide;
(b) N-(1Cyclohexa-1',4'-dienylethylpiperid-4-yl)-2-methoxy-4-acetamido-5-chlorobenzamide;
(c) N-[1-(4-Methylcyclohexa-1,4-dienyl)methylpiperid-4-yl]-2-methoxy-4-amino-5-chlorobenzamide;
(d) N-(1-Cyclohexa-1',4'-dienylmethylpiperid-4-yl)-2-methoxy-5-methylsulphonylbenzamide;
(e) N-(1-Cyclohexa-1',4'-dienylmethylpiperid-4-yl)-2-methoxy-5-chlorobenzamide;
(f) N-(1-Cyclohexa-1',4'-dienylmethylpiperid-4-yl)-2-methoxy-4-amino-5-bromobenzamide;
(g) N-(1-Cyclohexa-1',4'-dienylmethylpiperid-4-yl)-2-methoxy-5-sulphonamidobenzamide;
(h) N-[1-(1-Cyclohexa-1',4'-dienylethyl)piperid-4-yl]-2-methoxy-4-amino-5-chlorobenzamide;

(i) N-[1-(1-Cyclohexa-1',4'-dienylethyl)piperid-4-yl]-2-ethoxy-4-acetamido-5-chlorobenzamide;

(j) N-[1-(1-Cyclohexa-1',4'-dienylethyl)piperid-4-yl]-2-ethoxy-4-amino-5-chlorobenzamide;

(k) N-(1-Cyclohexa-1',4'-dienylmethylpiperid-4-yl)-2-methoxy-4,5-diaminobenzamide;

(l) N-(1-Cyclohexa-1',4'-dienylmethylpiperid-4-yl)-2-methoxy-4-dimethylamino-5-chlorobenzamide;

(m) N-(1-Cyclohexa-1',4'-dienylmethylpiperid-4-yl)-2-methoxy-4-methylamino-5-chlorobenzamide;

(n) N-(1-Cyclohexa-1',4'-dienylmethylpiperid-4-yl)-2-allyloxy-4-amino-5-chlorobenzamide;

(o) N-(1-Cyclohexa-1',4'-dienylmethylpiperid-4-yl)-2-ethoxy-4-amino-5-chlorobenzamide;

(p) N-(1-Cyclohexa-1',4'-dienylmethylpiperid-4-yl)-2-ethoxy-4-acetamido-5-chlorobenzamide;

(q) N-(1-Cyclohexen-3'-ylmethylpiperid-4-yl)-2-methoxy-4-amino-5-chlorobenzamide or a pharmaceutically acceptable acid addition salt thereof, or a mixture thereof, and a non-toxic pharmaceutically acceptable carrier or diluent.

33. A method for treating psychoses and allied conditions in which neuroleptic therapy is beneficial, which comprises administering a compound of claim 1 to a mammalian host, said compound being administered in an amount effective to prevent or ameliorate psychotic states.

34. A method for treating psychoses and allied conditions in which neuroleptic therapy is beneficial, which comprises administering a compound of claim 5 to a mammalian host, said compound being administered in an amount effective to prevent or ameliorate psychotic states.

35. A method for treating psychoses and allied conditions in which neuroleptic therapy is beneficial, which comprises administering a compound of claim 9 to a mammalian host, said compound being administered in an amount effective to prevent or ameliorate psychotic states.

36. A method for treating psychoses and allied conditions in which neuroleptic therapy is beneficial, which comprises administering to a mammalian host a compound selected from the following group:

(a) N-(1-Cyclohexa-1',4'-dienylmethylpiperid-4-yl)-2-methoxy-4-amino-5-chlorobenzamide;

(b) N-(1-Cyclohexa-1',4'-dienylmethylpiperid-4-yl)-2-methoxy-4-acetamido-5-chlorobenzamide;

(c) N-[1-(4-Methylcyclohexa-1,4-dienyl)methylpiperid-4-yl]- 2-methoxy-4-amino-5-chlorobenzamide;

(d) N-(1-Cyclohexa-1',4'-dienylmethylpiperid-4-yl)-2-methoxy-5-methylsulphonylbenzamide;

(e) N-(1-Cyclohexa-1',4'-dienylmethylpiperid-4-yl)-2-methoxy-5-chlorobenzamide;

(f) N-(1-Cyclohexa-1',4'-dienylmethylpiperid-4-yl)-2-methoxy-4-amino-5-bromobenzamide;

(g) N-(1-Cyclohexa-1',4'-dienylmethylpiperid-4-yl)-2-methoxy-5-sulphonamidobenzamide;

(h) N-[1-(1-Cyclohexa-1',4'-dienylethyl)piperid-4-yl]-2-methoxy-4-amino-5-chlorobenzamide;

(i) N-[1-(1-Cyclohexa-1',4'-dienylethyl)piperid-4-yl]-2-ethoxy-4-acetamido-5-chlorobenzamide;

(j) N-[1-(1-Cyclohexa-1',4'-dienylethyl)piperid-4-yl]-2-ethoxy-4-amino-5-chlorobenzamide;

(k) N-(1-Cyclohexa-1',4'-dienylmethylpiperid-4-yl)-2-methoxy-4,5-diaminobenzamide;

(l) N-(1-Cyclohexa-1',4'-dienylmethylpiperid-4-yl)-2-methoxy-4-dimethylamino-5-chlorobenzamide;

(m) N-(1-Cyclohexa-1',4'-dienylmethylpiperid-4-yl)-2-methoxy-4-methylamino-5-chlorobenzamide;

(n) N-(1-Cyclohexa-1',4'-dienylmethylpiperid-4-yl)-2-allyloxy-4-amino-5-chlorobenzamide;

(o) N-(1-Cyclohexa-1',4'-dienylmethylpiperid-4-yl)-2-ethoxy-4-amino-5-chlorobenzamide;

(p) N-(1-Cyclohexa-1',4'-dienylmethylpiperid-4-yl)-2-ethoxy-4-acetamido-5-chlorobenzamide;

(q) N-(1-Cyclohexen-3'-ylmethylpiperid-4-yl)-2-methoxy-4-amino-5-chlorobenzamide or a pharmaceutically acceptable acid addition salt thereof, or a mixture thereof, said compound being administered in an amount effective to prevent or ameliorate psychotic states.

* * * * *